(12) United States Patent
Kurz (10) Patent No.: US 7,752,929 B2
(45) Date of Patent: Jul. 13, 2010

(54) MASS VELOCITY AND AREA WEIGHTED AVERAGING FLUID COMPOSITIONS SAMPLER AND MASS FLOW METER

(75) Inventor: Jerome L. Kurz, Carmel Valley, CA (US)

(73) Assignee: Los Robles Advertising, Inc., Monterey, CA (US)

( * ) Notice: Subject to any disclaimer, the term of this patent is extended or adjusted under 35 U.S.C. 154(b) by 378 days.

(21) Appl. No.: 11/993,085

(22) PCT Filed: Jun. 21, 2006

(86) PCT No.: PCT/US2006/024133

§ 371 (c)(1),
(2), (4) Date: Dec. 19, 2007

(87) PCT Pub. No.: WO2007/002190

PCT Pub. Date: Jan. 4, 2007

(65) Prior Publication Data

US 2009/0223309 A1 Sep. 10, 2009

Related U.S. Application Data

(60) Provisional application No. 60/692,724, filed on Jun. 22, 2005.

(51) Int. Cl.
*G01N 1/00* (2006.01)
(52) U.S. Cl. ...................................................... 73/863
(58) Field of Classification Search .................... 73/863
See application file for complete search history.

(56) References Cited

U.S. PATENT DOCUMENTS

| | | | |
|---|---|---|---|
| 4,442,720 A | 4/1984 | Apley et al. | |
| 6,883,389 B2 | 4/2005 | Eldridge | |
| 6,904,815 B2 | 6/2005 | Widmer | |
| 6,976,397 B2 | 12/2005 | Widmer | |

*Primary Examiner*—Hezron Williams
*Assistant Examiner*—Alex Devito
(74) *Attorney, Agent, or Firm*—Patent Law Group LLP; David C. Hsia (57) ABSTRACT

A sampling device and method for use with a conduit for fluid which has at least one sampling nozzle or sample hole. The sample collected is directed to a manifold where an analysis is conducted and flow rates are measured. The sampled fluid is returned to the conduit. The Static Pressure Control System uses a vacuum pump or other device to equalize the static pressures of the sample nozzle collection manifold and the Static Pressure of the Conduit to achieve the mass-velocity and area-weighted average fluid composition and mass flow rate.

25 Claims, 4 Drawing Sheets

MASS VELOCITY AND AREA WEIGHTED AVERAGING FLUID COMPOSITIONS SAMPLER AND MASS FLOW METER

BACKGROUND OF THE INVENTION

1. Field of the Invention

The present invention is a sampling method and a device for obtaining real time, accurate measurements of the fluid composition and mass flow rates in conduits having uniform or non-uniform fluid composition, velocity and temperature profiles. The present invention includes the sampling of all fluids, including gases, aerosols, particulates, liquids and combinations of the same.

2. Description of Related Art

The problem of obtaining real-time accurate measurements of aerosol and gas in processes in conduits with uniform or non-uniform gas velocity, composition, temperature profiles, swirl and turbulence is a common one. Simply inserting a single-point gas sampling probe into a conduit of unknown characteristics only samples the fluid composition in one location which is not representative of the entire flow field in the conduit. The largest error is generally due to the velocity which can easily vary by a factor of five, the composition by a factor of three and temperature by 50% in combustion applications such as in a large coal-fired boiler, for example. In this example, measurement of the excess oxygen and carbon monoxide is a vital parameter to control combustion and improve plant efficiency. Measurement of the emission of particulates from all processes is very important for pollution control. The present invention can also be used to measure particulates as well.

The applicant is aware of the following references which relate to sampling and measurement of fluid flowing in a conduit.

| U.S. Pat. No. | Inventor(s) |
| --- | --- |
| 2,523,721 | Russell et al |
| 2,614,423 | Carbone |
| 4,115,229 | Capone |
| 4,290,315 | Grönberg |
| 6,164,142 | Dimeff |
| 6,642,720 | Maylotte et al |
| 6,843,104 | Busch |
| 6,862,915 | Staphanos et al |
| 2003/018,586 | Orieskie et al |

Russell et al disclose an apparatus for analyzing gaseous fuel before it is delivered into the heating chamber. A sample is collected and burned under controlled conditions. The combustion products are analyzed.

Carbone discloses the measurement of fluid flow through a conduit across the cross-sectional area of the conduit. The mean total differential between the impact pressure and the static pressure actuates a measuring and recording metering mechanism.

Capone discloses a gas analyzer for analysis of explosive mixtures. A correction loop flow circuit is used to bring a sample past a gas sensing element and back to a common inlet-outlet chamber.

Gröberg discloses an apparatus for determining the differential pressure and the volumetric fluid flow in a conduit. There is a pipe loop provided with a series of ports for sensing pressure.

Dimeff discloses an air flow measuring device which present a restricted orifice to the air flow and measure the pressure drop to determine the flow rate.

Maylotte et al disclose a wireless sensor assembly for measuring selected properties of a gas stream.

Busch discloses a system for measuring gaseous constituents in a flowing gas mixture. A mixing device in a flow homogenizes the gas mixture before it is detected by the sensor which detects individual gas constituents.

Staphanoes et al disclose a combustion gas analyzer for measuring the concentration of a gas constituent in an exhaust gas stream.

Orieskie et al disclose a process flow device which has a self-averaging orifice plate. The volumetric rate of flow is measured by a differential pressure process.

None of these references disclose a method of using one or more sampling nozzles which direct the fluid sample flow into a manifold wherein the flow rate and composition of the conduit fluid may be analyzed from a small sample stream of fluid having the same properties of the fluid in the conduit, nor a method in which the sample streams are collected independent of each other and collect a sample that represents the product of the fluid composition and the conduit mass flow rate at each nozzle or hole in the probe.

SUMMARY OF THE INVENTION

In one or more embodiments of the present disclosure, a device for sampling a fluid in a conduit includes sampling nozzles in the conduit, a sample collection manifold connected to the sampling nozzles, a manifold static pressure port on the sample collection manifold, conduit static pressure ports in the conduit, and a flow device in a sample path. The sampling nozzles are oriented into a flow of the fluid for sampling the fluid in an area of the conduit. The sample collection manifold collects and mixes sample streams of the fluid from the sampling nozzles. The sample collection manifold provides a sample flow of the fluid for the sample path. The manifold static pressure port provides a manifold static pressure inside the sample collection manifold. The conduit static pressure ports are located in the area of the conduit sampled by the sampling nozzles. The conduit static pressure ports provide a conduit static pressure in the area of the conduit sampled by the sampling nozzles. The flow device adjusts a flow rate of the sample flow such that the manifold static pressure is equal to the conduit static pressure. For such a device, a fluid composition in the sample path is a mass average composition of the area in the conduit sampled by the sampling nozzles, and a mass flow rate in the sample path is proportional to a mass average flow rate of the area in the conduit sampled by the sampling nozzles.

These and other objects of the present invention will become apparent from a reading of the following specification taken in conjunction with the enclosed drawings.

PRINCIPLE OF OPERATION

Figure 1:
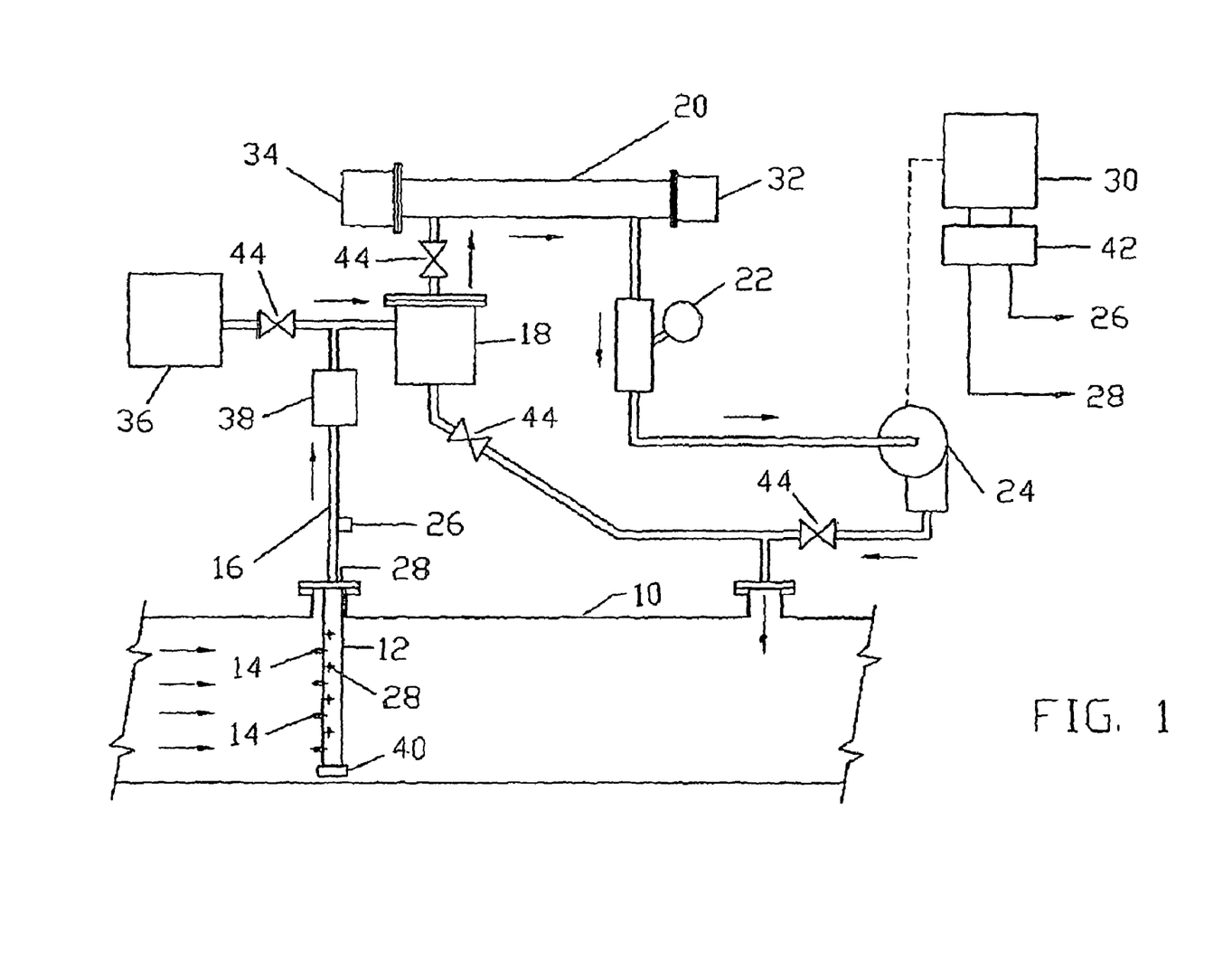
FIG. 1 is a diagram of the Sample Loop of the present invention.

FIG. 1 shows a simplified drawing of the preferred embodiment of a sampling loop for a single sampling probe assembly. Several such probe assemblies are required for large conduits. Each probe has sample nozzles located at the centroid of equal flow areas in the conduit 10. The number of sample nozzles and probes is determined by the severity of the non-uniform properties of the velocity, temperature and fluid composition profiles. The Sampling Probe 12 consists of one or more sample nozzles 14 connected to a Sample Nozzle Collection Manifold 16 in which the sampled streams mix and flow through the Particulate Analyzer 38 (if desired), the Particulate Filter 18 (if required), the Fluid Composition Measurement Chamber 20, Fluid Analyzers 32, 34 any other measurement devices, Mass Flow Meter 22 and Vacuum Pump 24 or equivalent device. The Sample Nozzle Collection Manifold 16 has Static Pressure Ports 26 mounted flush with the inside wall. The average Conduit Static Pressure Ports 28 are located on the surface of the outer wall of the sampling probe. The preferred embodiment takes advantage of the pressure distribution over a circular tube in cross-flow for which the Conduit Static Pressure occurs at an angle of about 35° on both sides of the flow stagnation point on a circular cylinder. The Conduit Static Pressure Ports 28 are used to obtain the average conduit static pressure. This method gives a very good average static pressure in the presence of swirl and non-axial fluid velocity components in the duct.

Figure 2:
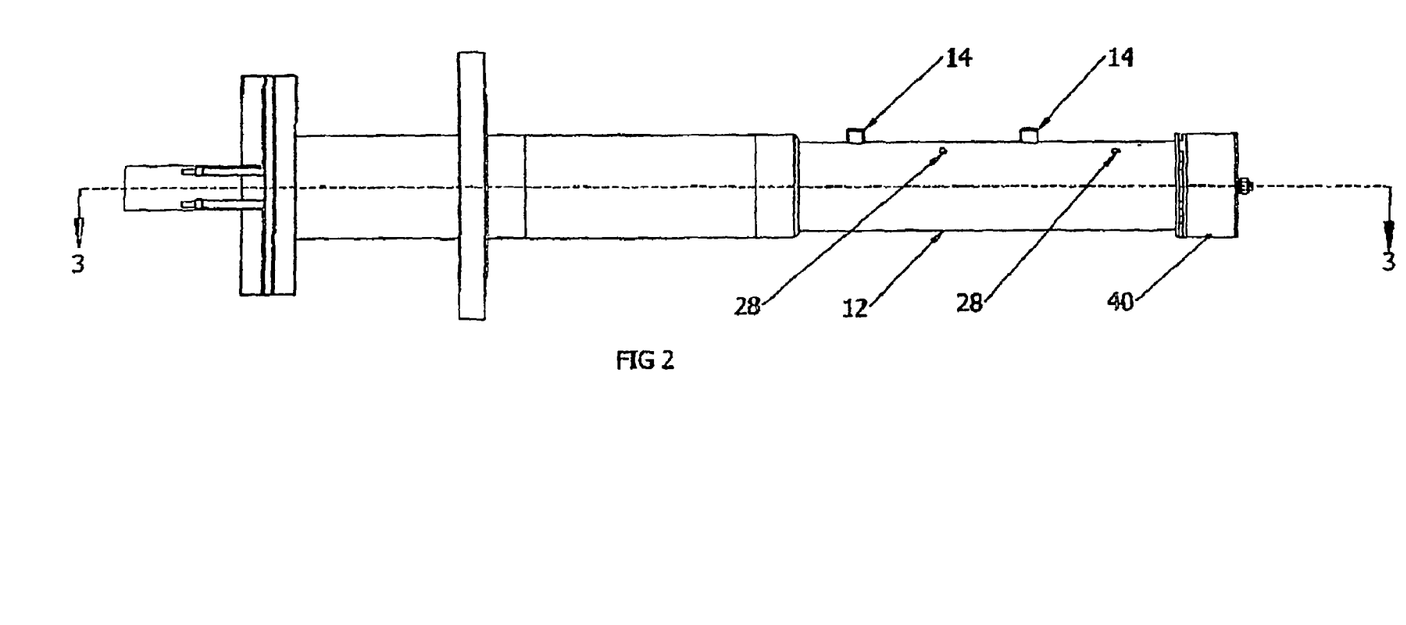
FIG. 2 is a top plan view of the Sampling Probe.

A simplified drawing of the internal structure of the Sampling Probe 12 is shown in FIG. 2 for a two-nozzle sampling system. The basic concept is to use the dynamic pressure of the fluid in the conduit to force a mass-velocity proportional sample flow into each nozzle. The sample stream from each nozzle is collected together and mixed in the Sample Nozzle Collection Manifold 16 and then flows into the Sample Loop depicted in FIG. 1. The following terms are applicable to FIG. 2.

$M = M_A + M_B$ = total mass flow of probe, nozzles $A$ & $B$ $M_A = \rho_A V_{A2} \times A$ = mass flow through nozzle $A$ $M_B = \rho_B V_{B2} \times A$ = mass flow through nozzle $B$ $V_{A2}$ is sample nozzle velocity at nozzle A
$V_{B2}$ is sample nozzle velocity at nozzle B $A_N$ = area of each flow nozzle = $\dfrac{\pi d^2}{4}$ d = sample nozzle internal diameter D = I.D. of sample collection manifold D >> d θ = static pressure port angle from stagnation point on circular cylinder $\rho_A$ = fluid density at nozzle A $\rho_B$ = fluid density at nozzle B $C_A, C_B$ = fluid concentrations at nozzles A, B $T_A, T_B$ = fluid temperatures at nozzles A, B $P_{SA1}$ = conduit stack pressure at nozzle A $P_{SB1}$ = conduit stack pressure at nozzle B $P_{sa2}$ = pressure at entrance to nozzle A $P_{SB2}$ = pressure at entrance to nozzle B $P_{SM}$ = static pressure of sample nozzle collection manifold $g_c$ = 32.15 ft/sec²

Figures 3, 4:
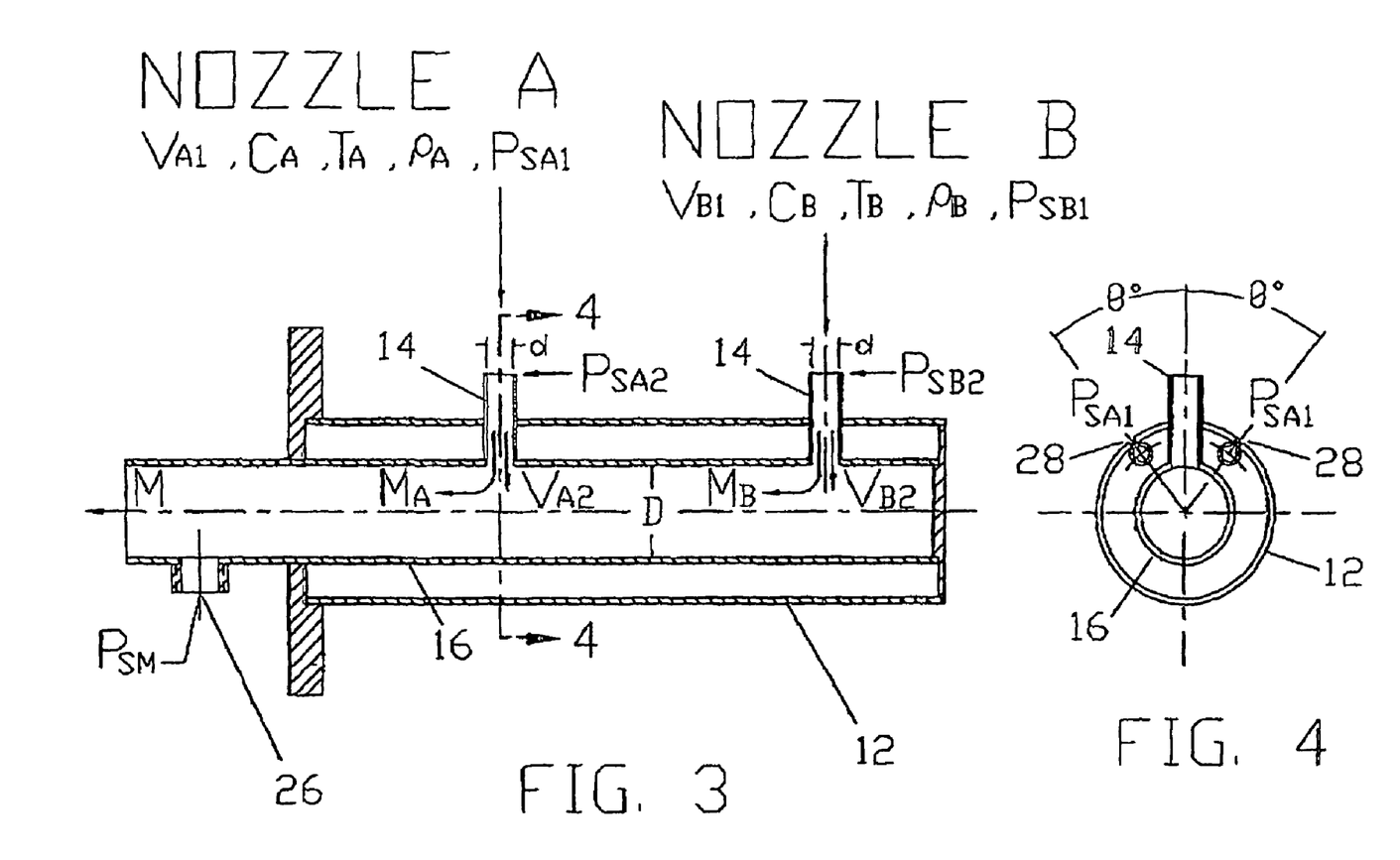
FIG. 3 is a cross-sectional view taken along the lines 3-3 of FIG. 2.
FIG. 4 is a cross-sectional view taken along the lines 4-4 of FIG. 3.

FIG. 3 is a drawing, (including definitions of all the variables) for a two-nozzle sample probe. Applying Bernoulli's Equation, the total pressure of the fluid streamlines at Nozzle A is:

$$P_{SA1} + \frac{1}{2}\frac{\rho_A V_{A1}^2}{g_c} = P_{SA2} + \frac{1}{2}\frac{\rho_A V_{A2}^2}{g_c} \qquad \text{Equation 1}$$

The available pressure difference to drive the sample flow into the sample nozzle and sample manifold is:

$$P_{SA2} - P_{SA1} = \frac{1}{2}\frac{\rho_A V_{A1}^2}{g_c} - \frac{1}{2}\frac{\rho_A V_{A2}^2}{g_c} \qquad \text{Equation 2}$$

If $V_{A2}=0$ then no flow can occur and the device functions as a Pitot Tube and responds to the average pressure in the Sample Nozzle Collection Manifold 16.

For sampling purposes, it is desired that the nozzle velocity $V_{A2}$ be proportional to the local conduit mass velocity $V_{A1}$. The sample flow through the nozzles and into the Sample Nozzle Collection Manifold 16 is dependent on the pressure of the Sample Nozzle Collection Manifold Static Pressure ($P_{SM}$). Therefore, the following equation applies:

$$P_{SA2} - P_{SM} = \frac{1}{2}\frac{\rho V_{A1}^2}{g_c} - \frac{1}{2}\frac{\rho V_{A2}^2}{g_c} \qquad \text{Equation 3}$$

The maximum sample flow rate occurs when the sample loop is "short-circuited". If $P_{SA2}-P_{SM}$ is forced to be equal to 0 then it is obvious that $V_{A1}=V_{A2}$ and the system is a self-driven linearly proportional sampler; however, there is a pressure drop caused by the sample nozzle. This pressure drop $\Delta P_n$ is shown in Equation 4:

$$\Delta P_n = C_D \left( \frac{1}{2}\frac{\rho_A V_{A2}^2}{g_c} \right) \qquad \text{Equation 4}$$

where $C_D$ is the nozzle pressure drop coefficient.

This pressure drop must be accounted for by subtracting it from the right-hand side of Equation 3 as shown below:

$$\begin{aligned}P_{SA2} - P_{SM} &= \frac{1}{2}\frac{\rho_A V_{A1}^2}{g_c} - \frac{\rho_A V_{A2}^2}{g_c} - C_D \frac{1}{2}\frac{\rho_A V_{A1}^2}{g_c} \\ &= \frac{1}{2}\frac{\rho_A V_{A1}^2}{g_c} - (1+C_D)\left(\frac{1}{2}\frac{\rho_A V_{A2}^2}{g_c}\right)\end{aligned} \qquad \text{Equation 5}$$

If we set $P_{SA2} - P_{SM} = 0$

Then $\dfrac{1}{2}\dfrac{\rho_a V_{A1}^2}{g_c} = (1+C_D)\dfrac{1}{2}\dfrac{\rho_A V_{A2}^2}{g_c}$ -continued $$V_{A2} = \frac{V_{A1}}{\sqrt{1+C_D}}$$ Equation 6

Equation 6 demonstrates that the method provides a sample nozzle velocity directly proportional to the local conduit velocity. Therefore, if the static pressure in the Sample Nozzle Collection Manifold is maintained equal to the Conduit Static Pressure the sample nozzle velocity $V_{A2}$ will be proportional to the local conduit velocity ($V_{A1}$). In practice $V_{A2}$ is about 90% of $V_{A1}$, for gases, for example.

Additional sample loop pressure drop caused by friction, bends, fittings, valves, Particulate Filter, Gas Composition Analyzers, Mass Flow Meter and will greatly affect the performance of the invention as the Sample Nozzle Manifold Static Pressure will rise above the conduit static pressure and cause the sample rate to decrease; and the nozzle velocity will not be proportional to the local conduit velocity, therefore, not meeting the desired average fluid concentration nor total duct mass flow rate. The solution to this problem and the essence of the present invention is to use a Vacuum Pump 24 or other suitable device to offset any sample loop pressure drops in order to obtain the same result as given in Equation 6. The other devices may be a jet eductor, a fan, a blower or other devices known to persons skilled in the art. By meeting the criteria the operators of each nozzle is independent of the other nozzles, which is a required condition for mass-velocity weighted composition measurements.

This is accomplished by using an Active Control System 30 in which the Differential Pressure Transmitter 42 measures the difference between the Sample Nozzle Collection Manifold Static Pressure Port 26 and the Conduit Static Pressure Ports 28 and controls the Vacuum Pump 24 (or other device) to increase or decrease the Sample Nozzle Collection Manifold Static pressure whereby offsetting any pressure drop in the Sample Loop.

Using Equation 5 and incorporating any additional sample loop pressure drop, ΔP, it can be shown that this invention solves the pressure drop interference problem:

$$P_{SA2} - P_{SM} = \frac{1}{2}\frac{\rho V_{A1}^2}{g_c} - \frac{1}{2}\frac{\rho V_{A2}^2}{g_c}(1+C_D) - \Delta P$$ Equation 7

ΔP=$P_{SM}$-$P_{SA1}$=The difference between the Sample Nozzle Collection Static Pressure Manifold and the Conduit Static Pressure, as defined previously.
Then:

$$P_{SA2} - P_{SM} = \frac{1}{2}\frac{\rho V_{A1}^2}{g_c} - \frac{1}{2}\frac{\rho V_{A2}^2}{g_c}(1+C_D) - P_{SM} + P_{SA1}$$

So that:

$$P_{SA2} - P_{SM} = \frac{1}{2}\frac{\rho V_{A1}^2}{g_c} - \frac{1}{2}\frac{\rho V_{A2}^2(1+C_D)}{g_c}$$ Equation 8

This gives the same result as Equation 5 which verifies that the Active Static Pressure Controller feature is essential to obtain a truly mass-velocity weighted fluid composition and mass flow rate measurement, and is the preferred embodiment of this invention.

Figure 5:
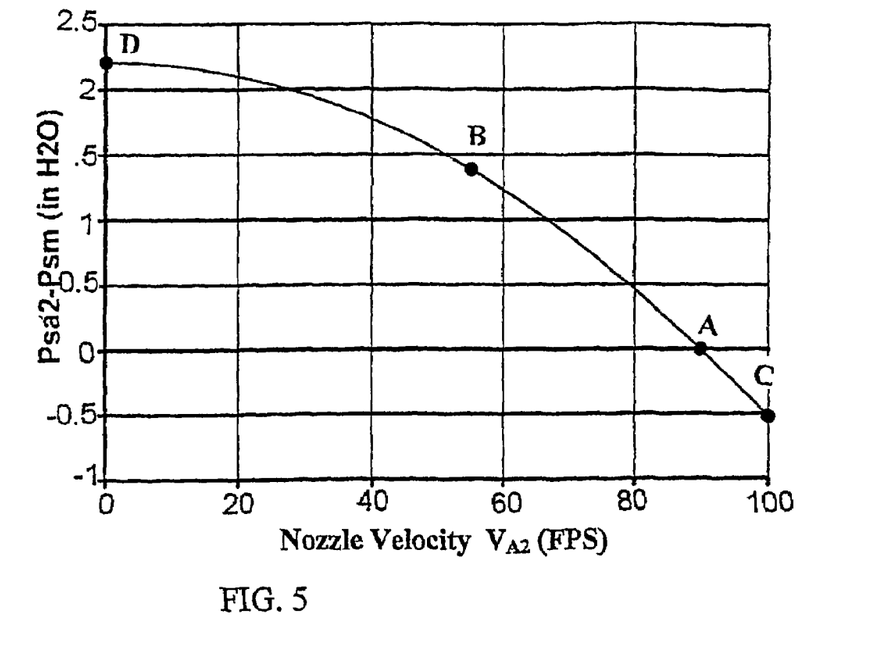
FIG. 5 is a graph showing the Operating Characteristics of the present invention.

Operating Characteristics:

FIG. 5 shows the operating characteristics of the present invention. The ordinate $P_{SA2}$-$P_{SM}$ is the difference between the pressure at the entrance to Nozzle A and the Sample Collection Manifold Static Pressure ($P_{SM}$). The abscissa ($V_{A2}$) is the velocity in the sample nozzle. FIG. 5 is a plot of Equation 8 previously described.

Figure 6:
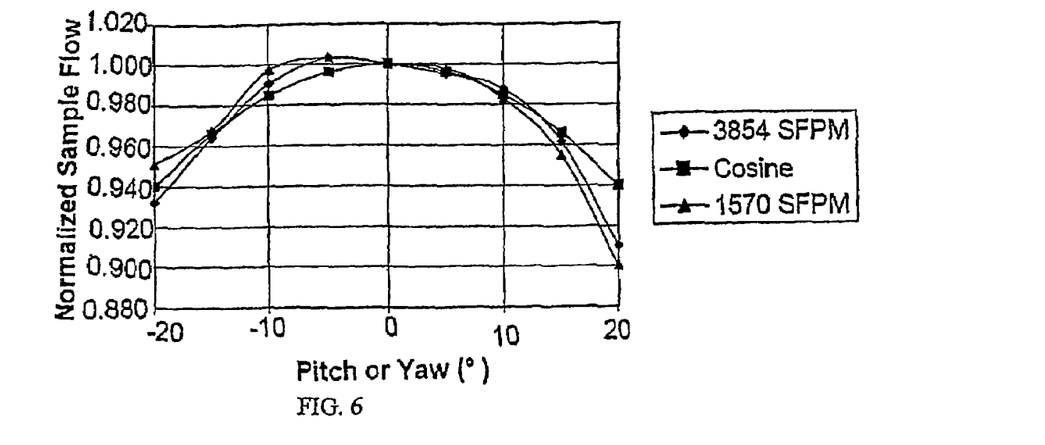
FIG. 6 is a graph showing Pitch and Yaw Data.

There are four operating modes for the present invention:
1) Mass-Velocity Proportional Sampling Mode
2) Under-Sampling Mode
3) Over-Sampling Mode
4) Pitot Tube Velocity Mode A) Mass-Velocity Proportional Sampling Mode: This mode uses an Active Control System to maintain the Sample Manifold Static Pressure equal to the Conduit Static Pressure by means of a vacuum pump 24 or other device. The operating point for this Mode is labeled A on FIG. 5. This insures that there is no flow circulation between sample nozzles 14, and that the various sample flows are independent of each other. The fluid composition is mass-velocity weighted at each sample nozzle and the mixture of all the sample inputs collected in the Sample Nozzle Collection Manifold 16 represents the true mass-velocity and conduit flow area-weighted sample for all fluid constituents. For gases, the velocity in the sample nozzles is about 90% of the local conduit velocity and the total sample flow is about 90% of the ideal sample flow. The velocity ratio can be experimentally determined so that knowing this ratio, the flow area of the conduit, the sample flow rate and the total sample nozzle area, the total mass-flow rate of the conduit can be accurately obtained over the entire range of operations. The sample nozzles in the preferred embodiment are insensitive to swirl and non-axial duct velocity components because of the nozzle design (FIG. 6).

TABLE 1

| Ref. Velocity (SFPM) | Sample (SCFM) | Pitch (°) | Normalized Sample | Cosine Response |
|---|---|---|---|---|
| 3854 | 2.766 | −20 | 0.932 | 0.940 |
| 3812 | 2.8613 | −15 | 0.964 | 0.966 |
| 3825 | 2.9403 | −10 | 0.991 | 0.985 |
| 3826 | 2.978 | −5 | 1.003 | 0.996 |
| 3823 | 2.9683 | 0 | 1.000 | 1.000 |
| 3812 | 2.954 | 5 | 0.995 | 0.996 |
| 3810 | 2.932 | 10 | 0.988 | 0.985 |
| 3804 | 2.854 | 15 | 0.961 | 0.966 |
| 3813 | 2.701 | 20 | 0.910 | 0.940 |
| 1576 | 1.0777 | −20 | 0.951 | 0.940 |
| 1570 | 1.0967 | −15 | 0.968 | 0.966 |
| 1575 | 1.1307 | −10 | 0.998 | 0.985 |
| 1580 | 1.137 | −5 | 1.003 | 0.996 |
| 1570.5 | 1.13343 | 0 | 1.000 | 1.000 |
| 1570 | 1.131 | 5 | 0.998 | 0.996 |
| 1577 | 1.1142 | 10 | 0.983 | 0.985 |
| 1570 | 1.08233 | 15 | 0.955 | 0.966 |
| 1570 | 1.02045 | 20 | 0.900 | 0.940 |

The essential feature of this preferred embodiment is that pressure drops created by the Fluid Composition Analyzers 32, 34, Particulate Filters 18, Sample Mass Flow meters 22 and any other pressure drop causing devices in the sample loop 10 can be canceled out provided that the Sample Manifold Static Pressure and the Conduit Static Pressure are equal to each other. This is the preferred embodiment for all situations for clean or dirty fluids.

B) Under-Sampling Mode: The operating range, labeled B on FIG. 5, is between the Pitot Tube Velocity Mode, labeled D on FIG. 5, and the Mass Velocity Proportional Sampling Mode, labeled A in FIG. 5. The Sample Nozzle Collection Manifold static pressure is higher than the Conduit Static Pressure such that the sample rate is lower and incorrect compared to the Mass-Velocity Proportional Mode. Lower velocity areas of the conduit will not be sampled properly, and flow circulation will occur between the nozzles, such that the sample flows from each nozzle are not independent of each other which is a necessity of this invention. This Mode is affected by pressure drops in the sample loop. This mode can only be used for certain applications in which the sample loop pressure drops are very small and constant over time.

C) Over-Sampling Mode: In this mode the Sample Manifold Static Pressure is much less than the Conduit Static Pressure, such that a larger sample flow rate is achieved due to a vacuum pump 24 or other device. There is a special condition in which the Active Control System can operate the sample system at an average isokinetic condition (nozzle velocity equals local conduit velocity) labeled C on FIG. 5, but not all sample nozzles will be isokinetic nor independent of each other. The samples are not mass-weighted.

D) Pitot Tube Velocity Mode: This mode is labeled as D on FIG. 5. The Sample Nozzle Collection Manifold 16 is shut-off so the sample flow rate is zero. This mode operates as a multi-point Pitot Tube which the average differential pressure minus the Conduit Static Pressure. These devices do not give the accurate average velocity reading due to internal circulation between the sample nozzles unless the velocity profile is very uniform. This mode is not a sampling mode and is included in this disclosure only to show the complete operating characteristics of the present invention method and devices.

Mass Flow Measurement Method:

The total mass flow rate for the conduit can be determined from the mass flow rate of one or more sampling assemblies that are appropriately located in the conduit and use the preferred embodiment. The ratio of the sample nozzle velocity to the conduit velocity is a function of the sample nozzle pressure drop coefficient ($C_D$) as shown in Equation 6. The total mass flow of the conduit for one sampling assembly as depicted for the two-nozzle sampling example of FIG. 3 is:

$$M_T = \left(\sqrt{1+C_D}\right)(M_A + M_B) \times \frac{A_C}{2A_N} \quad \text{Equation 9}$$

Where:

$M_T$=Total Sample Mass Flow Rate $C_D$=is experimentally determined nozzle pressure drop coefficient $M_A$=Mass Flow Rate through Nozzle A $M_B$=Mass Flow Rate through Nozzle B $A_C$=Flow Area of Conduit $A_N$=Area of each nozzle Effect of Non-Axial Conduit Velocity:

Several nozzle designs have been tested to find the best shape to produce the largest sample flow rate for the lowest nozzle pressure drop and have good pitch and yaw behavior. The ideal response is for the nozzle to have a "cosine" response to pitch and yaw angles of the velocity vector. Many nozzle shapes have been tested including rounded inlets, sharp-edge nozzle inlets, inside and/or outside tapered nozzle inlets and holes in the probe instead of nozzles. The preferred embodiment is a constant diameter nozzle having a rounded inlet at the nozzle tip protruding into the flow stream. The preferred embodiment is a good compromise between a having high sample nozzle velocity and pitch and yaw characteristics and dirt accumulations. When a protruding nozzle is used, it has been found that by having the nozzle tip extend from the probe surface one or two diameters better pitch and yaw performance are obtained. This is due to the fact that the pressure distribution around a circular tube probe structure changes very rapidly with angle, and when a nozzle with an extended tip is used, it is less affected by the probe structure.

FIG. 6 shows the pitch and yaw response data of the preferred embodiment compared to the ideal cosine response. This response is much better than most other fluid sampling devices known by the inventor.

The only accurate sampling mode is the Mass-Velocity Proportional Sampling Mode as described above although the present invention includes other modes of operation. It produces an independent sample rate at each nozzle, compensates for all pressure drops in the sample loop, has good off-axis velocity response characteristics and pneumatically performs the provides a mathematically correct fluid composition equations for the average fluid composition and the conduit mass flow rate over a wide range of fluid velocities, fluid composition, temperature, pressure, and dirty fluids.

DESCRIPTION OF THE PREFERRED EMBODIMENTS

A diagram showing the system of the present invention is shown in FIG. 1. The present invention is a mass-velocity weighted sampling probe and is used to obtain truly representative samples for the analyzers. The present invention pneumatically performs the mass-velocity and area averaging according to the following equation which is the correct definition of the True Concentration Average.

$$\overline{C_i} = \frac{\iint \rho(x,y)V(x,y)C(x,y)_i dx dy}{\iint \rho(x,y)V(x,y) dx dy}$$

Where:

$\overline{C_i}$ is the mass-velocity and area average concentration in the conduit of fluid component i, $\rho(x,y)$ is the fluid density, $V(x,y)$ is the fluid velocity and $C(x,y)$, is the concentration of Component i.

As shown in FIG. 1, a probe 12 is installed which extends perpendicularly into the conduit, vent, duct or stack 10 in which the measurements are to be taken. Preferably, a plurality of probes 12 are used to effectively sample over the area of the conduit. Each probe 12 is located at the centroid of equal flow area locations within the conduit. At least one, and preferably, a plurality of Sampling Nozzles 14 are mounted on each probe 12. The nozzles extend outwardly from the probe. The Sampling Nozzles 14 are oriented so that the flow of fluid within the conduit is directed into the opening in the nozzle. This opening communicates with the Sample Nozzle Collection Manifold 16. The number of Probes 12 and Sampling Nozzles 14 is determined by extent of the non-uniform properties of the velocity, temperature and fluid concentration profile in the conduit. Preferably, the plurality of probes and nozzles are arranged on a cross-sectional area of the conduit.

Thus, there is a least one Sampling Nozzle 14 placed at equal areas within the conduit facing the flow, each of which has a mass velocity that is linearly proportional to the local mass velocity of the fluid in the conduit such that the resulting flow rate from all the nozzles represents a truly representative sample of the aerosol and gases in the conduit. This sample flows through the Particulate Analyzer 38 (if used) the Particulate Filter 18 (if used) the Fluid Composition Measurement Chamber 20, the In-Line Mass Flow Meter 22, through the Vacuum Pump 24 (or other suitable device) and is exhausted back to the Conduit 10, thus completing the Sample Loop.

The mass rate of the Sample Loop is proportional to the mass flow rate for the area of the conduit being measured. One or more such multi-point sampling probe assemblies may be used to obtain the average fluid concentration and the mass flow rate of the entire conduit. The sum of the product of the mass flow rate and the concentration fluid constituent for each sampling probe assemblies divided by the number of sampling probe assemblies provides the mass-velocity weighted average concentration for each constituent that is being measured. The average mass flow rate of all the systems times the total area of the conduit times the nozzle velocity compared to the local conduit velocity provides an accurate and repeatable mass flow rate in the conduit as previously described in the Principle of Operation Section of the disclosure.

It is well known that elbows, obstructions and area changes in conduits cause swirl, turbulences and non-axial fluid velocity vectors. The shape of the sampling nozzles 14 for the preferred embodiment provide a good response to pitch and yaw angles of the velocity in the conduit compared to the ideal cosine response FIG. 6.

An important application for the present invention is for measuring and controlling the combustion process in fossil-fueled power plants. Accurate measurement of the excess Oxygen and Carbon Monoxide are required to optimize the efficiency. It is well known that fly ash is a major problem in coal-fired power plants. For such dirty applications, the preferred embodiment includes a Particulate Filter 18 in the Sample Loop. The filter cleans the sample fluid before it enters the Fluid Composition Measurement Chamber 20 and the Mass Flow Meter 22. All Sample Loop Pressure Drops are canceled by the Active Static Pressure Control 30 Embodiment.

The concentration of particulates in the Conduit 10 is measured by the Particulate Analyzer 38 which is placed in series with the Sample Nozzle Collection Manifold 16 and upstream of the Particulate Filter 18. Detection of any other fluid properties can be made by placing the appropriate analyzer in series with the Sample Nozzle Collection Manifold 16 either upstream or downstream of the Particulate Filter 18, as required.

The active Static Pressure Control System 30 uses a Differential Pressure Transmitter 42 to measure the difference between the Sample Nozzle Collection Manifold Pressure Port 26 and the Conduit Static Pressure Port 28 and controls the Vacuum Pump 24 (or other suitable device) to make this difference equal to zero. The active Static Pressure Control System 30 constitutes the essence of the present invention. FIG. 4 shows a cross section of the sampling probe and Conduit Static Pressure Ports.

The Mass Flow Meter 22 is located at the Sample Loop shown in FIG. 1. The preferred embodiment is an In-Line Thermal Mass Flow Meter having a low pressure drop and high flow turn down performance.

Another preferred embodiment of the present invention shown in FIG. 1 is the Air Purge Cleaning Controller 36 for dirty fluid applications. It uses a "blow-down" tank of compressed air that flows through a heater (if required) to clean the Particulate Filter 18, Sample Nozzle Collection Manifold 16, the Sample Nozzles 14, Sample Nozzle Manifold Static Pressure Ports 26 and Conduit Static Pressure Ports 28. The cleaning air with the collected dirt is discharged to the conduit. There is a Valve 40 mounted on the end of the probe 12 that opens up when the cleaning cycle is activated and allows the accumulated dirt to escape into the Conduit 10. Control Valves 44 are used to direct the purge air into the appropriate components and vent the purged air to the conduit.

The preferred embodiment utilizes a Fluid Analyzer Measurement Chamber 20 which is essentially a pipe in which the sample gas flows in at one end and out of the other end into the Mass Flow Meter 22. The Fluid Composition Analyzers 32, 34 are in-situ instruments that are usually inserted into a conduit. It is also possible to use extractive gas analyze similar to those used for US EPA CEM Stack Monitors by extracting the samples from the sample loop directly.

Obviously, many modifications may be made without departing from the basic spirit of the present invention. Accordingly, it will be appreciated by those skilled in the art that within the scope of the appended claims, the invention may be practiced other than has been specifically described herein.

The invention claimed is:

1. A device for sampling a fluid in a conduit, comprising:
    sampling nozzles in the conduit, the sampling nozzles being oriented into a flow of the fluid for sampling the fluid in an area of the conduit;
    a sample collection manifold connected to the sampling nozzles for collecting and mixing sample streams of the fluid from the sampling nozzles, the sample collection manifold providing a sample flow of the fluid for a sample path;
    a manifold static pressure port on the sample collection manifold, the manifold static pressure port providing a manifold static pressure inside the sample collection manifold;
    conduit static pressure ports in the conduit, the conduit static pressure ports being located in the area of the conduit sampled by the sampling nozzles, the conduit static pressure ports providing a conduit static pressure in the area of the conduit sampled by the sampling nozzles;
    a flow device in the sample path, the flow device adjusting a flow rate of the sample flow such that the manifold static pressure is equal to the conduit static pressure; and
    wherein a fluid composition in the sample path is a mass average composition of the area in the conduit sampled by the sampling nozzles, and a mass flow rate in the sample path is proportional to a mass average flow rate of the area in the conduit sampled by the sampling nozzles.

2. The device of claim 1, further comprising:
    fluid property measuring devices coupled serially in the sample path, the fluid property measuring devices determining properties of the fluid, the fluid property measuring devices causing a pressure change;
    a differential pressure transmitter coupled to (1) the manifold static pressure port to sense the manifold static pressure, and (2) the conduit static pressure ports to sense the conduit static pressure; and a controller coupled to (1) the differential pressure transmitter to sense a difference between the manifold and the conduit static pressures, and (2) the flow device to adjust the sample flow so the manifold static pressure is equal to the conduit static pressure in order to offset the pressure change.

3. The device of claim 2, wherein the sample collection manifold is located inside a cylindrical body, the conduit static pressure ports are defined on the cylindrical body, and the sampling nozzles extend from the sample collection manifold through the cylindrical body to form an integrated probe in the conduit.

4. The device of claim 3, wherein the conduit static pressure ports are located at a 35 degree angle to the flow of the fluid in the conduit.

5. The device of claim 2, wherein the fluid property measuring devices include at least one of a particulate analyzer, a composition sampling device, and a flow meter.

6. The device of claim 5, further comprising a particulate filter in the sample path, the particulate filter removing particulates in the fluid.

7. The device of claim 5, wherein the composition sampling device comprises a chamber and fluid analyzers at two ends of the chamber.

8. The device of claim 5, wherein the flow meter is a mass flow meter.

9. The device of claim 2, further comprising an air purge system connected to the sample path, the air purge system being operable to flush components of the device.

10. The device of claim 9, wherein the sample collection manifold comprises a distal end with a cleanout valve, the cleanout valve being operable to open when the air purge system flushes the components of the device.

11. The device of claim 1, wherein the flow device is selected from the group consisting of a vacuum pump, a jet eductor, a fan, and a blower.

12. The device of claim 1, further comprising an analyzer connected to the sample path, the analyzer extracting a portion of the fluid from the sample path to measure a property of the fluid.

13. The device of claim 1, wherein the sample path is coupled to the conduit to return the sample flow back into the conduit.

14. A method for sampling a fluid in a conduit, comprising:
sampling the fluid in an area of the conduit with sampling nozzles oriented into a flow of the fluid;
collecting and mixing sample streams of the fluid from the sampling nozzles in a sample collection manifold;
providing a sample flow of the fluid from the sample collection manifold to a sample path;
sensing a manifold static pressure in the sample collection manifold through a manifold static pressure port on the sample collection manifold;
sensing a conduit static pressure with conduit static pressure ports in the area of conduit sampled by the sampling nozzles;
adjusting the sample flow with a flow device in the sample path so that the manifold static pressure is equal to the conduit static pressure, said adjusting being based on said sensing; and
wherein a fluid composition in the sample path is a mass average composition of the area in the conduit sampled by the sampling nozzles, and a mass flow rate in the sample path is proportional to a mass average flow rate of the area in the conduit sampled by the sampling nozzles.

15. The method of claim 14, further comprising analyzing the fluid in the sample path using fluid property measuring devices coupled serially in the sample path, wherein the fluid property measuring devices cause a pressure change and said adjusting the sample flow so that the manifold static pressure is equal to the conduit static pressure to offsets the pressure change.

16. The method of claim 15, wherein said analyzing comprises at least one of determining a particulate in the fluid, determining a composition of the fluid, and determining a flow rate of the fluid.

17. The method of claim 16, further comprising filtering the particulate in the sample path.

18. The method of claim 16, wherein said determining a flow rate of the fluid comprises determining a mass flow rate.

19. The method of claim 18, wherein said determining a mass flow rate comprises determining the mass flow rate in the area of the conduit using the sample collection manifold with n nozzles as follows:

$$M_T = (\sqrt{1 + C_D})(M_P)\frac{A_C}{nA_N},$$

where $M_T$ is a mass flow rate in the area of the conduit, $C_D$ is a nozzle pressure drop coefficient, $M_P$ is a total sample mass flow in one of the sample collection manifold and the sample path, $A_c$ is a flow area of the conduit, n is a number of the sampling nozzles, and $A_N$ is an area of each nozzle.

20. The method of claim 19, wherein said determining a mass flow rate comprises determining the mass flow rate in the area of the conduit using the sample collection manifold with two nozzles as follows:

$$M_T = (\sqrt{1 + C_D})(M_A + M_B)\frac{A_C}{2A_N},$$

where $M_T$ is a mass flow rate in the area of the conduit, $C_D$ is a nozzle pressure drop coefficient, $M_A$ is a mass flow rate through a first nozzle, $M_B$ is a mass flow rate through a second nozzle, $A_c$ is a flow area of the conduit, and $A_N$ is an area of each nozzle.

21. The method of claim 15, further comprising flushing the sample path with an air purge system.

22. The method of claim 21, further comprising opening a cleanout valve at a distal end of the sample collection manifold during said flushing.

23. The method of claim 14, wherein said adjusting the sample flow with a flow device comprises one of increasing the sample flow to decrease the manifold static pressure and decreasing the sample flow to increase the manifold static pressure.

24. The method of claim 14, further comprising:
extracting a portion of the sample flow from the sample path; and
analyzing the portion of the sample flow to measure a property of the fluid.

25. The method of claim 14, further comprising returning the sample flow from the sample path back into the conduit.

* * * * *